(12) United States Patent
Millet

(10) Patent No.: US 10,980,772 B2
(45) Date of Patent: Apr. 20, 2021

(54) COMPOSITIONS AND METHODS FOR DELIVERING TETRAHYDROCANNABINOL AND KETONE BODIES

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

(21) Appl. No.: 16/272,328

(22) Filed: Feb. 11, 2019

(65) Prior Publication Data

US 2020/0061021 A1   Feb. 27, 2020

Related U.S. Application Data

(60) Provisional application No. 62/769,432, filed on Nov. 19, 2018, provisional application No. 62/760,462, filed on Nov. 13, 2018, provisional application No. 62/723,283, filed on Aug. 27, 2018.

(51) Int. Cl.

| A61K 31/352 | (2006.01) |
|---|---|
| A61K 47/10 | (2017.01) |
| A61K 47/14 | (2017.01) |
| A61P 25/04 | (2006.01) |
| A61P 29/00 | (2006.01) |
| A61P 35/00 | (2006.01) |
| A61P 25/24 | (2006.01) |
| A61K 31/19 | (2006.01) |

(52) U.S. Cl.
CPC ............ *A61K 31/352* (2013.01); *A61K 47/10* (2013.01); *A61K 47/14* (2013.01); *A61P 25/04* (2018.01); *A61P 25/24* (2018.01); *A61P 29/00* (2018.01); *A61P 35/00* (2018.01); *A61K 31/19* (2013.01)

(58) Field of Classification Search
CPC .................................................. A61K 31/351
USPC ........................................................ 514/456
See application file for complete search history.

(56) References Cited

U.S. PATENT DOCUMENTS

| 2,238,149 | A | 4/1941 | Aeckerle |
|---|---|---|---|
| 2,976,073 | A | 3/1961 | Russell et al. |
| 5,093,044 | A | 3/1992 | Wretlind |
| 5,116,868 | A | 5/1992 | Chen et al. |
| 5,654,266 | A | 8/1997 | Chen et al. |
| 5,700,670 | A | 12/1997 | Yamagishi et al. |
| 6,207,856 | B1 | 3/2001 | Veech |
| 6,316,038 | B1 | 11/2001 | Veech |
| 6,323,237 | B1 | 11/2001 | Veech |
| 6,380,244 | B2 | 4/2002 | Martin et al. |
| 6,613,356 | B1 | 9/2003 | Vlahakos |
| 6,706,756 | B1 | 3/2004 | Fitzpatrick et al. |
| 6,835,750 | B1 | 12/2004 | Henderson |
| 7,351,736 | B2 | 4/2008 | Veech |
| 7,807,718 | B2 | 10/2010 | Hashim et al. |
| 8,101,653 | B2 | 1/2012 | Veech |
| 8,124,589 | B2 | 2/2012 | Henderson |
| 8,426,468 | B2 | 4/2013 | Henderson |
| 8,642,654 | B2 | 2/2014 | Clarke et al. |
| 8,748,400 | B2 | 6/2014 | Henderson |
| 9,138,420 | B2 | 9/2015 | D'Agostino et al. |
| 9,211,275 | B2 | 12/2015 | Clarke et al. |
| 9,675,577 | B2 | 6/2017 | D'Agostino et al. |
| 9,717,767 | B2 | 8/2017 | Carpenter et al. |
| 9,795,580 | B2 | 10/2017 | Weeber et al. |
| 9,808,481 | B2 | 11/2017 | Ritter et al. |
| 9,957,246 | B2 | 5/2018 | Stinchcomb et al. |
| 10,022,409 | B2 | 7/2018 | Carpenter et al. |
| 10,051,880 | B2 | 8/2018 | Clarke et al. |
| 10,245,242 | B1 | 4/2019 | Millet |
| 10,245,243 | B1 | 4/2019 | Millet |
| 10,292,592 | B2 | 5/2019 | Marshall et al. |
| 10,588,877 | B2 | 3/2020 | Arnold |
| 10,660,958 | B2 | 5/2020 | Clarke |
| 2001/0014696 | A1 | 8/2001 | Veech |
| 2001/0041736 | A1 | 11/2001 | Veech |
| 2003/0022937 | A1 | 1/2003 | Veech |
| 2005/0129783 | A1 | 6/2005 | McCleary |
| 2007/0179197 | A1 | 8/2007 | Henderson |

(Continued)

FOREIGN PATENT DOCUMENTS

| CN | 1347319 | 5/2002 |
|---|---|---|
| EP | 2283834 | 2/2011 |

(Continued)

OTHER PUBLICATIONS

Haywood A, Glass BD. Pharmaceutical excipients—where do we begin? Australian Prescriber. 2011; 34: 112-114.
Dolson, Laura. How to Test Your Blood for Ketones. Downloaded Apr. 1, 2015. http://lowcarbdiets.about.com/od/KetogenicDiets/a/How-to-Test-Blood-For-Ketones.htm.
Nova Max Plus Glucose and Ketone Testing with One Monitor. Downloaded Apr. 1, 2015. http://www.novacares.com/nova-max-plus/.
Serum Ketones Test. MedlinePlus Medical Encyclopedia. Downloaded Apr. 1, 2015. http://www.nlm.nih.gov/medlineplus/ency/article/003498.htm.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.

(Continued)

*Primary Examiner* — Taina D Matos Negron
(74) *Attorney, Agent, or Firm* — Workman Nydegger

(57) ABSTRACT

Disclosed herein are "ketannabis" (or "ketonnabis") compositions including a combination of: (1) tetrahydrocannabinol (THC); (2) a ketone body component such as beta-hydroxybutyrate (BHB) and/or acetoacetate; and (3) a dietetically or pharmaceutically acceptable carrier. Also disclosed herein are methods of using such ketannabis compositions for producing desired physiological effects. The ketannabis compositions beneficially enhance the euphoric effects of THC without aggravating common side effects or even acting to reduce common side effects such as anxiety, disruption of short-term memory, appetite increases, heart rate increases, and blood pressure changes.

24 Claims, 2 Drawing Sheets

(56) References Cited

U.S. PATENT DOCUMENTS

| | | |
|---|---|---|
| 2008/0058416 A1 | 3/2008 | Greenwood et al. |
| 2008/0287372 A1 | 11/2008 | Henderson |
| 2009/0253781 A1 | 10/2009 | Veech |
| 2010/0041751 A1 | 2/2010 | Henderson |
| 2010/0197758 A1 | 8/2010 | Andrews et al. |
| 2010/0298294 A1 | 11/2010 | Clarke |
| 2012/0071548 A1 | 3/2012 | Veech |
| 2013/0079406 A1 | 3/2013 | Veech |
| 2015/0065571 A1 | 3/2015 | Clarke et al. |
| 2015/0132280 A1 | 5/2015 | Lopez et al. |
| 2016/0193173 A1 | 7/2016 | Clarke et al. |
| 2016/0256411 A1 | 9/2016 | Aung-Din |
| 2017/0020844 A1 | 1/2017 | Galinski |
| 2017/0172969 A1 | 6/2017 | D'Agostino et al. |
| 2017/0258745 A1 | 9/2017 | Millet |
| 2017/0266148 A1 | 9/2017 | D'Agostino et al. |
| 2017/0290792 A1 | 10/2017 | Cavaleri |
| 2017/0296501 A1 | 10/2017 | Lowery et al. |
| 2017/0298339 A1 | 10/2017 | Hanson et al. |
| 2017/0304564 A1 | 10/2017 | DeHaan et al. |
| 2018/0021274 A1 | 1/2018 | Arnold |
| 2018/0055797 A1 | 3/2018 | Llosa et al. |
| 2018/0057846 A1 | 3/2018 | LLosa et al. |
| 2018/0195096 A1 | 7/2018 | Veech et al. |
| 2019/0099394 A1 | 4/2019 | Ari et al. |
| 2019/0167613 A1 | 6/2019 | Millet |
| 2019/0313682 A1 | 10/2019 | Nagel |

FOREIGN PATENT DOCUMENTS

| | | | |
|---|---|---|---|
| EP | 2976073 A1 | | 1/2016 |
| EP | 3094321 A1 | | 11/2016 |
| JP | 11060434 | | 3/1999 |
| JP | 2002521330 | | 7/2002 |
| RU | 2345546 | | 4/2008 |
| WO | WO8703808 | | 7/1987 |
| WO | WO 98/41200 | | 9/1998 |
| WO | WO 03/070823 | | 8/2003 |
| WO | WO2005107724 | | 11/2005 |
| WO | WO2007115282 | | 10/2007 |
| WO | WO2008005818 | | 1/2008 |
| WO | WO2008021394 A2 | * | 2/2008 |
| WO | WO2008024408 | * | 2/2008 |
| WO | WO2011101171 | | 8/2011 |
| WO | 2013/150153 A1 | | 10/2013 |
| WO | WO2014153416 A1 | * | 9/2014 |
| WO | 2015/071811 A1 | | 5/2015 |
| WO | 2015/156865 A1 | | 10/2015 |
| WO | WO2016123229 | | 8/2016 |
| WO | WO 2017/208217 | | 12/2017 |
| WO | WO 2018/089863 | | 5/2018 |
| WO | WO2019018683 | | 1/2019 |
| WO | 2019/237152 A1 | | 12/2019 |

OTHER PUBLICATIONS

A New Toy Measuring Blood Ketones. Diet Doctor, Aug. 21, 2012. Dowloaded Apr. 1, 2015. http://www.dietdoctor.com/a-new-toy-measuring-blood-ketoones.
Precision Xtra vs. NovaMax Plus: Ketone Meter Evaluation. Jimmy Moore's Livin' La Vida Low Carb Blog. Downloaded Apr. 1, 2015. http://livinlavidalowcarb.com/blog/precision-xtra-vs-novamax-plus-ketone-meter-evaluation/15918.
Kirsch, Jr et al. "Butanediol Induced Ketosis Increases Tolerance to Hypoxia in the Mouse." Stroke 1980 vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Henderson, Samuel T. "Ketone Bodies as a Therapeutic for Alzheimer's Disease." Neurotherapeutics. Jul. 2008;5 3 3):470-80.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Krotkiewski, M. "Value of VLCD Supplementation with Medium Chain Triglycerides." I'nt J Obes Relat Metab Disord. Sep. 2001;25(9):1 39300.
PCT International Search Report and Written Opinion issued by the International Searching Authority on Jul. 15, 2014 or International Patent Application No. PCT/US2014/031237.
Bastin et al., "Salt Slection and Optimisation Procedures for Pharmaceutical New Chemical Entities", American Chemical Society and The Royal Society of Chemistry, vol. 4, No. 5, 2000, pp. 427-435.
Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).
Parker, Steve, "Ketogenic Mediterranean Diet: Version 2.3," Nov. 23, 2010, pp. 1-3. (Year: 2010).
Sajewicz et al. in Journal of Liquid Chromatography & Related Technologies, 33:1047-1057 (2010) (Year: 2010).
Shigeno etal. in Biosci. Biotech. Biochem., 56(2), 320-323 (1992) (Year: 1992).
Optical Purity and Enantiomeric Excess at https://www.masterorganicchemistry.com/2017/02/24/optical-purity-and-enantiomeric-excess/. (Retrieved from the Internet Nov. 6, 2018) (Year: 2018).
Tisdale, "Reduction of weight loss and tumour size in a cachexia model by a high fat diet", British Journal of Cancer, Jul. 1987, vol. 56, p. 39-43.
U.S. Appl. No. 14/455,385, filed Jan. 2, 2015, Office Action.
U.S. Appl. No. 14/860,092, filed Mar. 9, 2016, Office Action.
U.S. Appl. No. 14/860,092, filed Oct. 17, 2016, Office Action.
U.S. Appl. No. 15/610,668, filed Jul. 25, 2018, Office Action.
U.S. Appl. No. 15/454,157, filed Jan. 11, 2018, Office Action.
U.S. Appl. No. 15/454,157, filed Jun. 13, 2018, Office Action.
U.S. Appl. No. 15/936,820, filed Nov. 14, 2018, Office Action.
U.S. Appl. No. 15/936,849, filed Nov. 14, 2018, Office Action.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
International Search Report cited in PCT/US19/27214 dated Jun. 25, 2019.
Written Opinion cited in PCT/US19/27214 dated Jun. 25, 2019.
U.S. Appl. No. 15/454,157, filed Feb. 26, 2019, Notice of Allowance.
U.S. Appl. No. 15/936,849, filed Jan. 24, 2019, Notice of Allowance.
Pubchem, "Acetoacetic acid" Electronic Resource: https://pubchem.ncbi.nim.nih.gov/compound/Acetoacetic-acid, Retrieved on Sep. 3, 2019.
Arendash et al. "Caffeine and Coffee as Therapeutics Against Alzheimer's Disease", Journal of Alzheimer's Disease 20, 2010, S117-S126.
Kesl, et al., "Effects of exogenous ketone supplementation on blood ketone, glucose, triglyceride, and lipoprotein levels in Sprague-Dawley rats", Nutrition & Metabolism (2016).
Extended European Search Report issued in PCT/US2017021886 dated Oct. 17, 2019.
International Search Report and Written Opinion issued in PCT/US19/48364 dated Nov. 15, 2019.
International Search Report and Written Opinion issued in PCT/US19/48357 dated Nov. 18, 2019.
U.S. Appl. No. 16/272,359, filed Feb. 11, 2019, Notice of Allowance.
U.S. Appl. No. 16/381,202, filed Oct. 22, 2019, Office Action.
U.S. Appl. No. 16/224,485, filed Nov. 27, 2019, Notice of Allowance.
U.S. Appl. No. 16/224,408, filed Nov. 27, 2019, Notice of Allowance.
International Search Report cited in PCT/US18/62093 dated Feb. 1, 2019.
International Search Report cited in PCT/US18/62096 dated Feb. 11, 2019.

(56) References Cited

OTHER PUBLICATIONS

Vandenberghe et al. in Can. J. Physiol. Pharmacol. 95: 455-458 (2017) (Published at www.nrcresearchpress.com/cjpp on Nov. 25, 2016). (Year: 2016).
Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.
Holtzman et al., "Role of adenosine receptors in caffeine tolerance", J. Pharmacol. Exp. Ther., 1991 ;256(1 ):62-68.
International Search Report and Written Opinion received for PCT Patent Application No. PCT/US20/37289, dated Sep. 30, 2020, 8 pages.
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Non-Final Office Action received for U.S. Appl. No. 16/381,202, dated Aug. 11, 2020, 8 pages.
Non-Final Office Action received for U.S. Appl. No. 16/720,211, dated Oct. 28, 2020, 14 pages.
Non-Final Rejection dated Sep. 9, 2020 for U.S. Appl. No. 16/783,956.
Notice of Allowance received for U.S. Appl. No. 16/381,202, dated Nov. 10, 2020, 8 pages.
Office Action cited in U.S. Appl. No. 16/720,211 dated Oct. 28, 2020.
Office Action cited in U.S. Appl. No. 16/996,509 dated Oct. 26, 2020.
Parker, Steve, "Ketogenic Mediterraanean Diet: Version 2.3," Nov. 23, 2010, pp. 1-3. (Year: 2010).
Requirement for Restriction/Election received for U.S. Appl. No. 16/551,570, dated Sep. 28, 2020, 6 pages.
International Search Report and Written Opinion received for PCT Patent Application No. PCT/US2020/033159, dated Aug. 12, 2020, 9 pages.
International Search Report and Written Opinion issued in PCT/US20/16952 dated Apr. 22, 2020.
International Search Report and Written Opinion issued in PCT/US20/17555 dated May 4, 2020.
International Search Report and Written Opinion issued in PCT/US20/17556 dated May 4, 2020.
International Search Report and Written Opinion issued in PCT/US20/17552 dated May 4, 2020.
Karppanen, H., et al, "Why and how to implement sodium, potassium, calcium, and magnesium changes in food items and diets?"
U.S. Appl. No. 16/409,501, filed Jan. 14, 2020, Notice of Allowance.
U.S. Appl. No. 16/272,145, filed Jan. 10, 2020, Office Action.
Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.
First Examination Report for New Zealand Patent Application No. 711433 issued by the New Zealand Intellectual Property Office dated Mar. 10, 2016.
First Office Action issued by the Chinese State Intellectual Property Office on Nov. 4, 2016 for corresponding Chinese Patent Application No. 201480016818.0.
Hashim, Sarni A., et al., "Ketone body therapy: from the ketogenic diet to the oral administration of ketone ester", Journal of Lipid Research, vol. 55, 2014.
Karppanen et al, J. Human Hypertension (2005), vol. 19, pp. S10-S19. (Year: 2005).
Murray, Andrew J., et al. "Novel ketone diet enhances physical and cognitive performance", The FASEB Journal, Vo. 30 Dec. 2016.
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Veech, et al., "Ketone Bodies Mimic the Life Span Extending Properties of Caloric Restriction", IUBMB Life Feb. 8, 2017.
Vorgerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.

\* cited by examiner

COMPOSITIONS AND METHODS FOR DELIVERING TETRAHYDROCANNABINOL AND KETONE BODIES

CROSS-REFERENCE TO RELATED APPLICATIONS

This Application claims priority to and the benefit of U.S. Provisional Patent Application No. 62/769,432, filed Nov. 19, 2018, and to U.S. Provisional Patent Application No. 62/760,462, filed Nov. 13, 2018, and to U.S. Provisional Patent Application No. 62/723,283, filed Aug. 27, 2018, the disclosures of which are incorporated herein by reference in their entireties.

BACKGROUND

Ketosis

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation of ketone bodies for energy. This metabolic state is called "ketosis".

Ketone bodies can be used by cells of the body as a fuel in addition or instead of glucose to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. Between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake to maintain a ketogenic metabolic state.

While in ketosis, the body is essentially burning fat for its primary fuel. The body initially cleaves fats into fatty acids and glycerol. It then transforms fatty acids into acetyl coenzyme A ("acetyl-CoA") molecules, which are then eventually transformed through ketogenesis into the water-soluble ketone bodies beta-hydroxybutyrate ("β-hydroxybutyrate" or "BHB"), acetoacetate, and acetone in the liver. BHB and acetoacetate are the ketone bodies used by the body for energy while acetone is removed as a by-product of ketogenesis. Although BHB is technically not a ketone, it is still referred to as a "ketone body" in the context of ketosis.

The metabolism of ketone bodies is associated with several beneficial effects. However, despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis through depleting glucose stores in the body is through fasting combined with exercise. This is physically and emotionally demanding and is extremely challenging even for the most motivated and disciplined.

Additionally, the transition into ketosis is often accompanied by hypoglycemia which can cause lethargy and light-headedness in many, resulting in an uncomfortable physiological and mental state commonly referred to as the "low-carb flu" or "keto flu." In addition, many people experience a down regulation in their metabolism as the body goes into an "energy-saving" mode. Some suggest that these transitory symptoms may last as long as two to three weeks. During this transition period, if any meal or snack consisting of carbohydrates over the restrictive amount is consumed, there is a rapid termination of ketogenesis, causing the body to exit from its state of ketosis as the body shifts back to glucose utilization as its primary fuel. At this point, the difficult transition into ketosis must begin anew. Thus, despite the potential of a ketogenic diet for weight loss and other health benefits, serious limitations continue to hinder the full realization of its potential.

Tetrahydrocannabinol

Tetrahydrocannabinol (THC) is one of the major cannabinoid constituents of the cannabis plant. The particular type found in cannabis is (−)-trans-$\Delta^9$-tetrahydrocannabinol, though the more generic term THC may also refer to isomers such as stereoisomers and double bond isomers. THC is the major cannabinoid component responsible for the psychoactive effects of cannabis. It is typically the most abundant constituent of the flower/bud portion of the cannabis plant.

THC is currently used as an active ingredient in medicines intended to increase appetite, reduce nausea, and alleviate neuropathic pain and spasticity. THC is most commonly administered orally or via inhalation. THC is believed to interact with a variety of biological targets, including cannabinoid receptors such as $CB_1$ and $CB_2$ as well as neurotransmitter receptors such as the μ- and δ-opioid receptors. The psychoactive effects of THC are believed to result from inhibition of adenylate cyclase, which leads to a decrease in the concentration of cyclic adenosine monophosphate (cAMP).

Though THC has several positive uses, with other uses likely to be discovered in the future, some limitations are currently known to exist. Though feelings of euphoria are often associated with use of THC, users may also experience adverse side effects, such as anxiety, panic attacks, increased heart rate, and changes in blood pressure. Thus, despite benefits associated with THC as a supplement or drug, several limitations to its use remain.

BRIEF SUMMARY

Disclosed herein are compositions including a combination of: (1) tetrahydrocannabinol (THC), precursor, and/or metabolite thereof; (2) a ketone body component such as beta-hydroxybutyrate (BHB) and/or acetoacetate; and (3) optionally a dietetically or pharmaceutically acceptable carrier. For ease of reference, such combination compositions may be referred to herein as "ketannabis compositions" and "ketonnabis compositions," which are each a portmanteau of "ketone" and "cannabis." Also disclosed herein are methods of using such ketannabis compositions for producing desired physiological effects in a mammal.

The administration of a ketannabis composition may provide a variety of beneficial physiological effects. In particular, the combined administration of a ketone body component and a THC component can provide one or more of: the reduction or elimination of THC side effects; the reduction or elimination of ketone body and/or ketosis side effects; and the enhancement of positive effects associated with THC and/or ketone bodies.

A ketannabis composition may lead to more efficient utilization of THC as compared to THC not combined with exogenous ketone bodies. For example, the euphoric effects may be higher for a given dose of a ketannabis composition than for THC not combined in a composition with exogenous ketone bodies. At the same time, the negative side effects of THC may not be correspondingly aggravated and may even be reduced when administered with exogenous ketone bodies. For example, the level of negative effects (such as appetite increases, anxiogenic effects, short-term memory disruption, heart rate increases, and blood pressure changes) may be lower for a given dose of a ketannabis composition than for a composition having the same amount of THC but without exogenous ketone bodies.

In some embodiments, a ketannabis composition has a broader range of effective dosages than THC without ketone bodies. Because the ketone bodies potentiate the utilization of THC, the positive effects may be realized at lower doses relative to the same amount of THC without ketone bodies. At the same time, the ketone bodies counteract one or more negative side effects of THC and thereby allow higher doses of THC before such negative side effects become excessive. Ketannabis compositions are therefore believed to expand the useful working range, or "sweet spot" of THC dosing, by providing enhanced positive effects and/or reducing negative side effects.

In some embodiments, a ketannabis composition lessens the negative side effects that can sometimes occur with ketone body supplementation. For example, the THC component of a ketannabis composition may reduce or eliminate symptoms of keto flu and/or symptoms of depression sometimes associated with attempts to enter a metabolic state of ketosis.

In some embodiments, the THC component and the ketone body component of a ketannabis composition can synergistically act to promote one or more positive effects. These positive effects may include one or more of neuroprotection, anti-inflammation, analgesic effects, antioxidant effects, anti-tumorigenic effects, and anti-aging effects.

Ketannabis compositions described herein may be provided as a solid, powder, liquid, gel, or other dietetically or pharmaceutically acceptable form. The compositions can be administered as a dietary supplement mixed with food or drink, in the form of one or more capsules or tablets, or in liquid form such as a mouth spray or energy shot, for example.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

Figure 1:
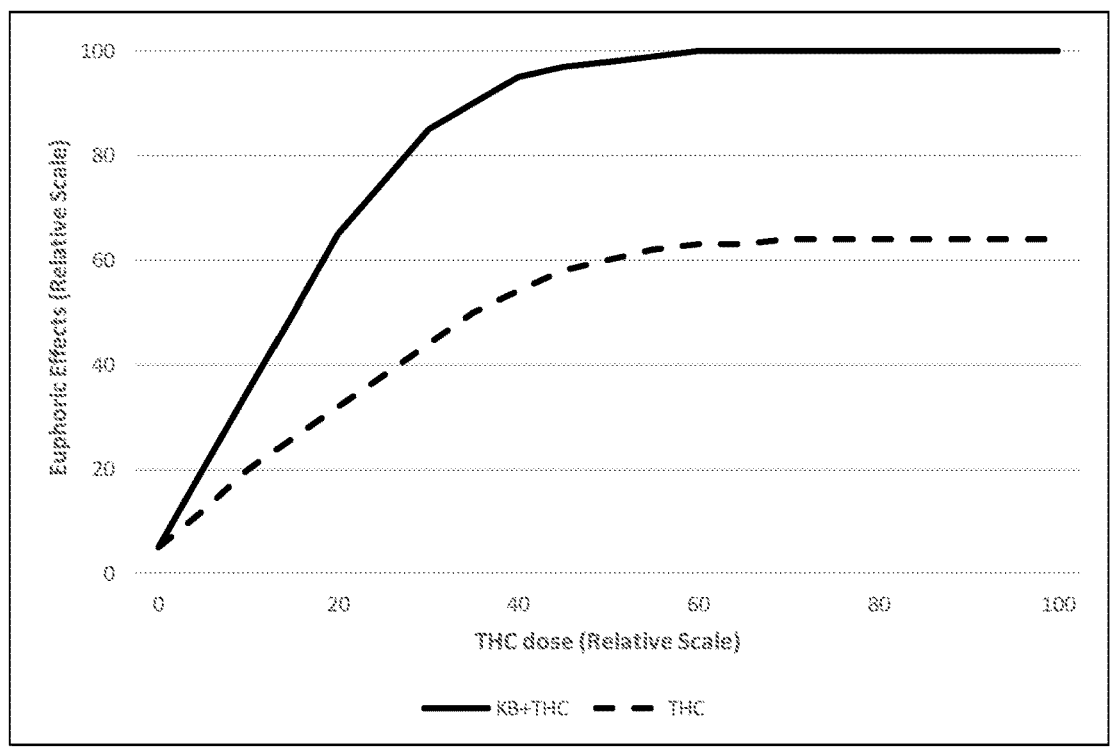
FIG. 1 schematically illustrates expected relative euphoric effects at different THC dosing levels comparing a composition of ketone bodies and THC to a composition of THC without ketone bodies.

The compound "tetrahydrocannabinol" or "THC" is one of the major cannabinoid constituents of the cannabis plant and is shown in Formula I (stereoisomers thereof may also be utilized):

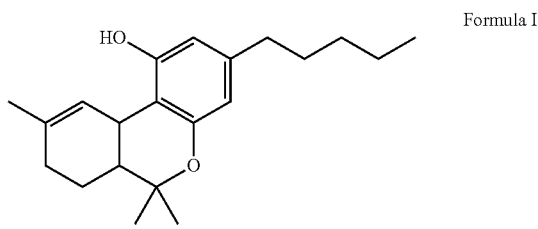 [SMILES: CCCCCc1cc(O)c2c(c1)OC(C)(C)C1CCC(C)=CC21]

Formula I

The term "ketone body" refers to compounds capable of being utilized by the body as an energy source and includes the compounds beta-hydroxybutyrate (BHB) and acetoacetate. Ketone body precursors may additionally or alternatively be utilized in the compositions described herein. Suitable ketone body precursors include, but are not limited to, 1,3-butanediol, medium chain fatty acids, and esters of medium chain fatty acids such as medium chain triglycerides. Ketone body compounds and ketone body precursor compounds are described in more detail below.

The compound "beta-hydroxybutyrate," also known as β-hydroxybutyrate, 3-hydroxybutyrate, βHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure of Formula II represents BHB compounds that may be utilized in the disclosed compositions:

Formula II where,
X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

BHB may be utilized by a patient's body as an energy source during instances of low glucose levels in the subject or when a patient's body is supplemented with a usable form of BHB. Although not technically a "ketone", one of skill in the art will recognize that BHB, in the context of ketosis, is commonly referred to as a "ketone body."

BHB is a chiral compound and can exist as the R-enantiomer or the S-enantiomer, a racemic mixture, or a mixture where one of the enantiomers is enriched relative to the other. Endogenous BHB produced by the body is the R-enantiomer and therefore the form that is more readily available as a ketone body. BHB can be transformed by the body into acetoacetate, which is not chiral, and acetoacetate can be transformed by the body into the R-enantiomer. It is believed that the S-enantiomer of BHB can be transformed into the R-enantiomer by first being converted into acetoacetate and then into the R-enantiomer.

The compound "acetoacetate" is the deprotonated form of acetoacetic acid, which is a carboxylic acid having the formula $CH_3COCH_2COOH$. The deprotonated form present at typical biological pH levels is therefore $CH_3COCH_2COO^-$. As stated above, the body can transform BHB into acetoacetate and vice versa. As with BHB, acetoacetate may be utilized as an energy source during ketosis. The general chemical structure of Formula III represents acetoacetate compounds that may be utilized in the disclosed compositions (stereoisomers thereof may also be utilized):

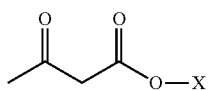

Formula III where,
X can be hydrogen, metal ion, amino cation, such as from an amino acid, alkyl, alkenyl, aryl, or acyl.

As with BHB, acetoacetate may be utilized by a patient's body as an energy source during instances of low glucose levels in the subject or when a patient's body is supplemented with a usable form of acetoacetate. Unlike BHB, acetoacetate is a true "ketone", and in the context of ketosis is commonly referred to as a "ketone body" along with BHB.

BHB and acetoacetate compounds are preferably provided in salt and/or ester form, although they can also be administered in acid form, or as a mixture of salt, ester and/or acid forms. Exemplary salt forms include sodium, potassium, calcium, magnesium salts, and lithium. Some embodiments include one or more transition metal salts. Transition metal cations suitable for use as part of a salt include chromium, manganese, cobalt, copper, zinc, iron, (e.g., as an iron II or iron III cation), molybdenum, and selenium. Other suitable salt forms include cations of organic compounds capable of having a net positive charge, including amino acids or their derivatives/metabolites such as arginine, lysine, leucine, iso-leucine, histidine, ornithine, creatine, agmatine, L-glutamine, and citrulline.

L-arginine is also known to promote formation of nitric oxide (NO) in the blood, which can help heart patients and men with erectile dysfunction. Other natural substances that can boost blood NO levels and improve quality of erection include beets, citrus (orange, lemon, grapefruit), pomegranate, dark chocolate, walnuts, arugula, spinach, watermelon, meat, seafood, garlic, cordyceps, maca root, panax ginseng, eleuthero root, rhodiola rosea, moringa leaf, yerba mate, goosefoot, safed musli, desmodium, spirulina, pycnogenol, hawthorn extract, icariin, grape seed extract, vitamin D, L-citrulline, and horny goat weed. PDE5 inhibitors can also be used to treat heart patients and erectile dysfunction. Examples include avanafil, lodenafil, mirodenafil, sildenafil, tadalafil, vardenafil, udenafil, zaprinast, icariin, benzamidenafil, and dasantafil.

Suitable ester forms of BHB include mono-esters of ethanol, mono-esters of 1-propanol, mono-esters of 1,3-propanediol, di-esters of 1,3-propanediol, mono-esters of S-1,3-butanediol, mono-esters of R-1,3-butanediol, di-esters of 1,3-butanediol, mono-esters of glycerin, di-esters of glycerin, and tri-esters of glycerin. 1,3-butanediol is a metabolic BHB precursor that may be additionally or alternatively be utilized as a source of BHB and/or acetoacetate compounds. The acid form of BHB and acetoacetate typically have an unpleasant taste but can be used by appropriate taste masking mechanisms, such as one or more capsules, tablets, or other bolus.

The beta-hydroxybutyrate and acetoacetate compositions may be provided in three general forms: 1) a salt form, 2) an ester form, and 3) a free acid form (i.e., beta-hydroxybutyric acid and acetoacetic acid). The compositions described herein may be provided in any one of these forms or as a mixture combining at least two of these forms.

Each of the different forms has its own properties and its own potential benefits and limitations. For example, ester forms of beta-hydroxybutyrate typically have poor organoleptic properties relative to the other forms of beta-hydroxybutyrate. That is, ester forms of beta-hydroxybutyrate are often described as having a pungent taste and/or smell.

Salt forms of beta-hydroxybutyrate are generally considered to taste better than ester forms. However, administration of clinically or dietetically effective doses of beta-hydroxybutyrate and/or acetoacetate in salt form inherently requires administration of relatively high levels of the corresponding cations. Sodium, for example, is often used as the cation in beta-hydroxybutyrate salts, and high levels of sodium have well-known negative health effects. Although different salts having different cations may be mixed to dilute the impact of a single cation, it can still be difficult to provide effective amounts of ketone bodies without upsetting the electrolyte balance in the subject/patient.

The free acid form of beta-hydroxybutyrate (i.e., beta-hydroxybutyric acid) and/or acetoacetate (i.e., acetoacetic acid) may also be utilized. However, because of the relatively low pKa values (e.g., beta-hydroxybutyric acid has a pKa of 4.70), these compounds deprotonate and produces $H^+$ at physiological pH. The resulting excess acidity can cause undesirable side effects including causing or aggravating gastrointestinal issues such as ulcers or reflux.

Combining different forms of beta-hydroxybutyrate can beneficially limit the occurrence and/or severity of these undesirable side-effects and/or can permit administration of higher doses of ketone bodies. For example, a combined form can deliver the same amount of ketone bodies as a single form without causing the same occurrence and/or severity of side-effects. Likewise, a combined form can deliver a greater amount of ketone bodies than a single form before reaching similar occurrence and/or severity of side-effects.

In other words, for a given dose of beta-hydroxybutyrate and/or acetoacetate, a combined form, and in particular the triple form, is expected to have less 1) organoleptic side-effects, 2) electrolyte imbalance side-effects, and/or 3) acidity side-effects as compared to the single form. For example, a single form ester may have a threshold dosage that the typical user will not exceed because of the negative organoleptic side-effects, a single form salt may have a threshold dosage limited by the recommended dietary limits of the electrolytes administered with the salt, and a single form acid may have a threshold dosage that the typical user will not exceed because of the negative effects of acidity. The combined forms, and in particular the triple form, may allow supplementation of greater amounts of ketone bodies without exceeding any of the thresholds related to organoleptic, electrolyte, or acidity side-effects.

In some embodiments, a triple form ketone body component includes at least about 2% of the ester form, at least about 2% of the salt form, and at least about 2% of the free acid form on a molar basis of beta-hydroxybutyrate and/or acetoacetate. In other words, at least about 2% of the number of ketone body molecules (beta-hydroxybutyrate and/or acetoacetate) are provided by each separate form. More preferably, a triple form includes at least about 5% ester form, at least about 5% salt form, and at least about 5% free acid form on a molar basis of ketone bodies, or at least about 10% ester form, at least about 10% salt form, and at least about 10% free acid form on a molar basis of ketone bodies, or at least about 20% ester form, at least about 20% salt form, and at least about 20% free acid form on a molar basis of ketone bodies, or at least about 30% ester form, at least about 30% salt form, or at least about 30% free acid form on a molar basis of ketone bodies.

In some embodiments, a triple form ketone body component includes an ester form at about 2% to about 96%, or about 5% to about 90%, or about 10% to about 80%, or about 20% to about 60% on a molar basis of ketone bodies, includes a salt form at about 2% to about 96%, or about 5% to about 90%, or about 10% to about 80%, or about 20% to about 60% on a molar basis of ketone bodies, and includes an acid form at about 2% to about 96%, or about 5% to about 90%, or about 10% to about 80%, or about 20% to about 60% on a molar basis of ketone bodies.

It is also possible to form an ester between BHB and THC, in which the carboxyl group of a BHB molecule is esterified with the hydroxyl group of a THC molecule. Such ester forms of BHB and THC can be used to provide a stabilized ketannabis compound. With such an ester compound, the ratio of BHB to THC is 1:1. The composition can also be enriched with additional BHB and/or THC molecules to provide other ratios of BHB to THC. Formula IV represents an exemplary BHB and THC ester (stereoisomers thereof may also be utilized).

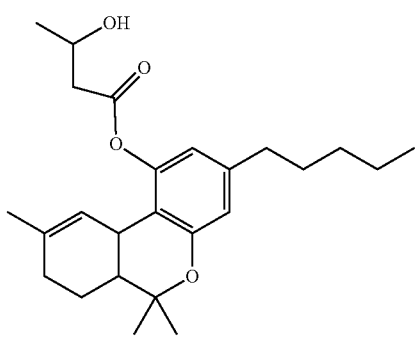

Formula IV

Similarly, it is possible to form an ester between acetoacetate and THC, in which the carboxyl group of an acetoacetate molecule is esterified with the hydroxyl group of a THC molecule. Such ester forms of acetoacetate and THC can be used to provide a stabilized compound. With such an ester, the ratio of acetoacetate to THC will be 1:1. The ester can also be enriched with additional acetoacetate and/or THC molecules to provide other ratios of acetoacetate to THC. Formula V represents an exemplary acetoacetate and THC ester (stereoisomers thereof may also be utilized).

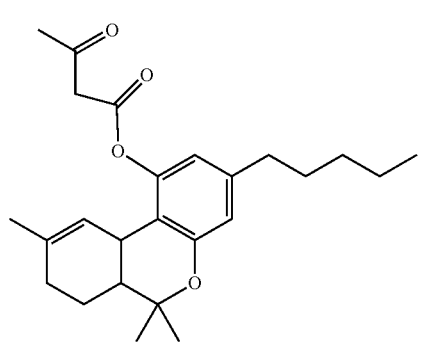

Formula V

Providing the compound in an ester form may beneficially enhance the solubility and/or bioavailability of the compound. For example, the esterified forms of CBD as described herein may have reduced hydrophobicity relative to non-esterified CBD. Such esters may be formed using known esterification techniques such as, for example, Fischer esterification.

The BHB compound can be provided as a racemic mixture of enantiomers, sometimes referred to DL-beta-hydroxybutyrate (alternatively RS-beta-hydroxybutyrate), which can be made synthetically. In humans, the enantiomer D-3-hydroxybutyrate ("D-beta-hydroxybutyrate", "D-BHB", "R-hydroxybutyrate" or "R-BHB") is synthesized in the liver from acetoacetate, the first ketone produced when in a state of ketosis. Therefore, it may be desirable to provide BHB as the enantiomer D-3-hydroxybutyrate to increase potency, either enriched relative to L-3-hydroxybutyrate ("L-beta-hydrobutyrate", "L-BHB", "S-beta-hydrobutyrate" or "5-BHB") or isolated from L-3-hydroxybutyrate. Alternatively, it may be desirable to provide BHB as the enantiomer L-3-hydroxybutyrate to increase potency, either enriched relative to D-3-hydroxybutyrate or isolated from D-3-hydroxybutyrate. Administering D-3-hydroxybutyrate, the endogenous form, results in attaining rapid elevated ketosis, while administering L-3-hydroxybutyrate, which must first be converted D-3-hydroxybutyrate, may provide slower and more sustained ketosis. D-3-hydroxybutyrate is also referred to as "R-beta-hydroxybutyrate" and L-3-hydroxybutyrate is also referred to as "S-beta-hydroxybutyrate."

As used herein, a "ketannabis composition" refers to a combination composition that includes: (1) THC and/or a precursor or metabolite thereof; (2) a ketone body component such as beta-hydroxybutyrate (BHB) and/or acetoacetate; and (3) optionally a dietetically or pharmaceutically acceptable carrier. The major metabolite of THC is 11-hydroxy-THC (i.e., 11-hydroxy-Δ9-tetrahydrocannabinol). The major precursor of THC within the cannabis plant is tetrahydrocannabinolic acid (THCA). THCA includes an additional carboxyl group that is believed to readily undergo decarboxylation to produce THC. Though the examples provided herein will typically refer only to THC, it will be understood that direct precursor compounds such as THCA and direct metabolite compounds such as 11-hydroxy-THC may additionally or alternatively be used as the respective component of the ketannabis composition.

As used herein, "subject," "patient," or "user" refers to mammals, including humans and other primates. The subject may be any mammal requiring metabolic therapy, treatment, or prophylaxis, or any mammal suspected of requiring metabolic therapy, treatment, or prophylaxis. Prophylaxis means that regiment is undertaken to prevent a possible occurrence, such as where a high risk of diabetes or other metabolic disorder is identified. "Patient," "subject," and "user" are used interchangeably herein.

"Ketosis" as used herein refers to a subject having blood ketone levels within the range of about 0.5 mmol/L to about 16 mmol/L. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis," or it denotes an altered metabolism in which fat becomes the predominant energy source, consequently shifting the body from a state of fat storage to a state of fat oxidation.

The term "administration" or "administering" is used herein to describe the process in which the ketogenic compositions are delivered to a subject. The composition may be administered in various ways including oral, intragastric, nasal or pulmonary, parenteral (referring to intravenous and intra-arterial and other appropriate parenteral routes), as an injectable, as a suppository, etcetera.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, dropper, spoon, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

II. Ketannabis Compositions

Ketannabis compositions described herein comprise: (1) THC and/or a precursor or metabolite thereof; (2) a ketone body component such as beta-hydroxybutyrate (BHB) and/ or acetoacetate; and (3) optionally a dietetically or pharmaceutically acceptable carrier.

Some ketannabis compositions may include one or more other cannabinoids in addition to or as an alternative to THC. For example, some embodiments may include amounts of cannabidiol (CBD), tetrahydrocannabivarin (THCV), cannabigeriol (CBG), cannabidivarin (CBDV), cannabichromene (CBC), cannabinol (CBN), cannabielsoin (CBE), iso-THC, cannabicyclol (CBL), cannabicitran (CBT), cannabivarin (CBV), cannabichromevarin (CBCV), cannabigerovarin (CBGV), cannabigerol monomethyl ether (CBGM), other cannabis-derived cannabinoids, a carboxylic acid form thereof, and combinations thereof. Some embodiments may intentionally omit one or more non-CBD cannabinoids such as CBD in order to enhance THC's effects.

For example, THCV can used to assist with weight loss, treat symptoms associated with diabetes, assist with treating anxiety and post traumatic stress disorder (PTSD), and treat neuro-disorders. CBG can be used to treat pain and inflammation, increase anti-oxidant levels, help skin disorders (psoriasis/acne), is anti-fungal, and helps with neuro-disorders. CBC can be used to block pain and inflammation, provide synergy with other cannabinoids (entourage effect), and promote anandamide (the bliss molecule). CBN can be used as a powerful sedative, to help increase appetite, help treat psoriasis, as an analgesic, and as an anti-convulsant and anti-emetic.

Ketannabis compositions described herein may also include one or more additional non-cannabinoid terpenes and/or terpenoids in addition to the cannabinoid component. For example, certain compositions may include one or more terpenes and/or terpenoids associated with the cannabis plant, such as alpha-pinene, myrcene, limonene, caryophyllene, linalool, humulene, ocimene, and terpinolene. Such terpenes and/or terpenoids may be utilized along with the cannabinoid component to modulate bioavailability and/or neuroavailability of the cannabinoid component via the entourage effect.

Although most of the ketannabis examples described herein utilize THC, some embodiments may substitute one or more related cannabinoids, including one or more of those described above, as an alternative to the THC component. In particular, some embodiments may include one or more cannabinoids that are structurally and/or functionally related to THC, such as those that are cyclized from a precursor compound (e.g., CBG or CBGV) in a way that maintains a single hydroxyl group.

Just as the THC may be provided as an ester where the THC molecule is bonded with a ketone body (e.g., a BHB or acetoacetate group), other cannabinoids included in the composition may also be provided in an ester form that combines the cannabinoid molecule with one or more ketone body moieties via an ester bond, such as by bonding the carboxyl group(s) of one or more ketone bodies to one or more available hydroxyl groups of the cannabinoid. For example, some embodiments may include CBD in addition to THC. The CBD may be provided as an ester by bonding one or both of the hydroxyl groups of the CBD with the carboxyl group of a ketone body (e.g., BHB or acetoacetate).

In one embodiment, the cannabinoid component includes THCV and/or its corresponding carboxylic acid THCVA, where the THCV is provided either as a free molecule in combination with one or more ketone bodies or as a compound bonded to a ketone body via an ester bond. THCV is structurally similar to THC. THCV includes a shorter propyl group rather than the longer pentyl group of THC. THCV may synergistically work with ketone bodies to provide one or more of appetite suppression, blood sugar regulation, anxiolytic effects, neuroprotection, and bone growth.

A ketannabis composition may also optionally include a supplemental source of ketone body precursors such as one or more of 1,3-butanediol, fatty acids, and/or esters of fatty acids. A typical ester form of fatty acids is a mono-, di-, or triglyceride. Preferred forms of fatty acids and their esters are medium chain fatty acids and medium chain triglycerides (MCT), though short and/or long chain fatty acids and their esters may also be utilized. In embodiments where used, a medium chain fatty acid has from 6 to 12 carbons, preferably from 8 to 10 carbons. Compositions and methods related to the combination of BHB with a medium chain fatty acid, or ester thereof, are disclosed in U.S. Pat. No. 9,138,420, which patent is incorporated herein by this reference in its entirety. Such compounds may be utilized as the ketone body component of the ketannabis compounds described herein.

Exemplary fatty acids are caprylic acid, also known as octanoic acid, comprising 8 carbon molecules, and capric acid, also known as decanoic acid, comprising 10 carbon molecules. Because MCTs are ketone body precursors, including one or more MCTs may provide an additional source for the production of ketone bodies independent of the BHB and acetoacetate compounds, thus helping to promote sustained elevation of ketone levels to a desired therapeutic level. The term "short chain triglycerides" (SCT) refers to molecules similar to MCT molecules but with short chain fatty acids (less than 6 carbon atoms in length) attached to the glycerol backbone. The term "long chain triglycerides" (LCT) refers to molecules similar to MCT molecules but with long chain fatty acids (more than 12 carbon atoms in length) attached to the glycerol backbone.

Examples and sources of the medium chain fatty acid, or an ester thereof such as a medium chain triglyceride, include coconut oil, coconut milk powder, fractionated coconut oil, palm oil, palm kernel oil, caprilic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

When medium chain fatty acids, fatty acid esters, or mono-, di- or triglycerides of medium chain fatty acids are provided, the composition is preferably administered such that the weight ratio of ketone bodies to medium chain fatty acid (or ester thereof) ranges from about 4:1 to about 1:4, or from about 2:1 to about 1:2, or from about 1.5:1 to about 1:1.5. The same ratios may be used when short chain fatty acids (or esters thereof) or long chain fatty acids (or esters thereof) are additionally or alternatively used.

In alternative embodiments, the compositions may further include one or more short and/or long chain fatty acids, fatty acid esters, or mono-, di- or triglycerides of short and/or long chain fatty acids in order to provide an additional source of ketone bodies for sustaining ketosis. In some embodiments, the composition is preferably administered such that the ratio of BHB/acetoacetate to medium, short and/or long chain fatty acid (or ester thereof) ranges from about 4:1 to about 1:4, or from about 2:1 to about 1:2, or from about 1.5:1 to about 1:1.5.

Examples of short chain fatty acids include acetic acid, propionic acid, butyric acid, isobutyric acid, valeric acid, isovaleric acid, and caproic acid. Examples of medium chain fatty acids include caprylic acid, capric acid, and lauric acid. Examples of long-chain fatty acids include lauric acid, myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

As described above, ketannabis compositions may be formulated with various ratios of ketone body component to THC. Ketannabis compositions may also be formulated with various ratios of different forms of ketone bodies to one another. That is, some embodiments may include a greater proportion of BHB relative to acetoacetate, whereas other embodiments may include a greater proportion of acetoacetate relative to BHB. For example, the BHB to acetoacetate ratio may be about 0.1:1, 0.25:1, 0.5:1, 0.75:1, 1:1, 1.25:1, 1.5:1, 2:1, 4:1, 9:1, or may be within a range having any two of the foregoing ratios as endpoints. The ratio may be formulated according to particular application needs and preferences. For example, BHB-based ketannabis compositions are believed to have greater relative effect on metabolic activity (e.g., fat loss, anti-inflammation) while acetoacetate-based ketannabis compositions are believed to have greater relative effect on neurological activity (e.g., neuroprotection, anxiolytic and anti-depressant effects, memory protection).

Thus, where the primary intended effects are metabolic in nature, a ketannabis composition may be formulated so that BHB makes up at least about 50%, or at least about 75%, or at least about 95%, or even about 100% of the content of the ketone body component of the ketannabis composition. On the other hand, where the primary intended effects are neurological in nature, a ketannabis composition may be formulated so that acetoacetate makes up at least about 50%, or at least about 75%, or at least about 95%, or even about 100% of the content of the ketone body component of the ketannabis composition.

III. Treatment Effects

The administration of a ketannabis composition may provide a variety of beneficial physiological effects. In particular, the combined administration of a ketone body component and a THC component can provide one or more of: the reduction or elimination of THC side effects; the reduction or elimination of ketone body and/or ketosis side effects; and the enhancement of positive effects associated with THC and/or ketone bodies.

THC supplementation has many potential benefits, including the promotion of a euphoric state characterized by an alteration in conscious perception, feelings of well-being, relaxation, increased appreciation of humor, music, and art, increased sensuality and libido, and increased metacognition and introspection. THC may also mimic endocannabinoids such as anandamide and thereby modulate the endocannabinoid system (ECS). The ECS is involved with regulation of a variety of different physiological systems and is believed to play a role in promoting homeostasis and equilibrium among the various physiological system.

Despite these benefits, THC can at times act as a "double-edged sword" by causing an overactive state characterized by anxiety/panic, increased heart rate, and changes in blood pressure (see, e.g., Jones "Cardiovascular system effects of marijuana" J. Clin. Pharmacol. 42 (11): 58-63; "Medical Marijuana and the Mind" Harvard Mental Health Letter, April 2010). Some people report experiencing paranoia when consuming THC-containing products. These anxiogenic and cardiovascular effects are typically the direct opposite of the effects intended.

Further, THC is well known to be associated with an increased appetite. While promoting the "munchies" may be desirable in some circumstances, such as patients with cancer or other terminal illnesses with depressed appetite, increased appetite can be an undesirable side effect because it can lead to weight gain and other poor dietary habits. THC use is also associated with disruption in short-term memory formation (see, e.g., Riedel et al. "Cannabinoid Function in Learning, Memory and Plasticity" Handbook of Experimental Pharmacology 168 (168): 445-477).

Beneficially, the supplementation of exogenous ketone bodies with THC can enhance the positive effects of THC without aggravating its negative side effects or even reducing negative side effects. In addition, THC can enhance positive effects of exogenous ketone bodies while reducing negative side effects sometimes associated with achieving and/or sustaining ketosis. Further, modulation of the ECS via THC dosing may be enhanced through the metabolic and/or molecular signaling effects of exogenous ketone bodies, which can therefore lead to a variety of beneficial physiological effects, particularly those related to immune system activities and inflammation regulation.

FIG. 1 schematically illustrates more efficient utilization of THC when combined with exogenous ketone bodies. As shown, the level of positive effects (shown here as "euphoric effects" on a relative scale of 0 to 100) are higher for a given dose of a ketannabis composition (KB+THC) than for a composition having the same amount of THC but without a ketone body component (THC).

Without being bound to any particular theory, it is believed that THC is more readily utilized when combined with a ketone body component as compared to when utilized without a ketone body component. In other words, it is believed that the ketone body component effectively "primes" the subject for more metabolically efficient utilization of consumed lipids. The exogenous ketone bodies may also induce a sustained state of ketosis, where the lipid-based metabolic efficiencies may be even further bolstered. THC, as a lipid itself, is therefore believed to have enhanced pharmacokinetics (e.g., more effective absorption, transport, cell permeation, etc.) when the subject is actively utilizing ketone bodies as an energy source, particularly when the subject is in a state of ketosis as opposed to a regular state of (primarily) glycolysis. For example, administration of THC to a subject in combination with exogenous ketone bodies, where preferably the subject is also in a state of elevated and/or sustained ketosis as a result of supplementation with ketone bodies, may result in about 10%, 20%, 40%, or 75% or more higher utilization of the THC as compared to THC supplementation without a ketone body component.

Figure 2:
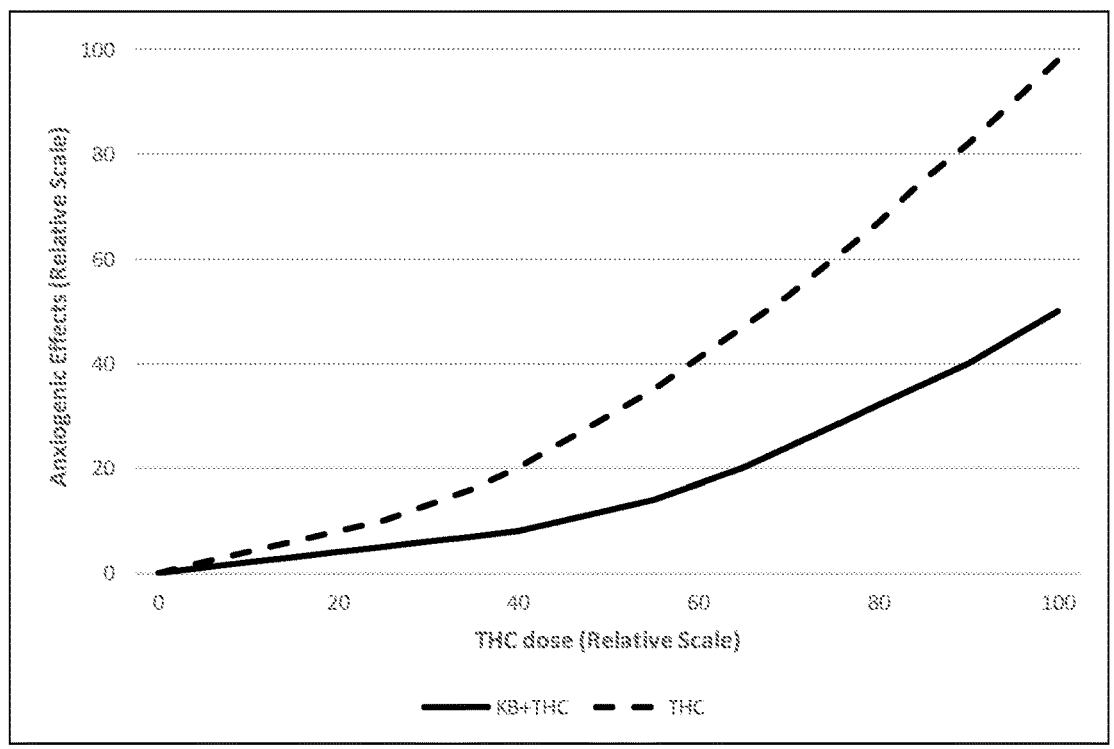
FIG. 2 schematically illustrates expected relative anxiogenic effects at different THC dosing levels comparing a composition of ketone bodies and THC to a composition of THC without ketone bodies.

Notwithstanding the enhancement of the positive effects of THC when administered with a ketone body component, the negative side effects of THC are not correspondingly aggravated and may even be reduced when administered with a ketone body component. FIG. 2 schematically illustrates reduced negative effects of THC when combined with a ketone body component. As shown, the level of negative effects (shown here as "anxiogenic effects" on a relative scale of 0 to 100) are lower for a given dose of a ketannabis composition (KB+THC) than for a composition having the same amount of THC but without a ketone body component (THC).

It is believed that even though THC is more effectively utilized by the body when combined with ketone bodies, other countervailing mechanisms are enough to counteract any corresponding enhancement of the negative side effects of THC or even reduce them. As explained in more detail below, the exogenous ketone body component may function to suppress appetite, reduce anxiety, protect cardiovascular health, and/or enhance memory. These effects are believed to beneficially counteract the negative effects of THC to effectively void any increases otherwise caused by the enhanced utilization of THC. In some circumstances, the countervailing effects of the ketone body component may even reduce the overall severity and/or occurrence of these negative effects.

Figure 3:
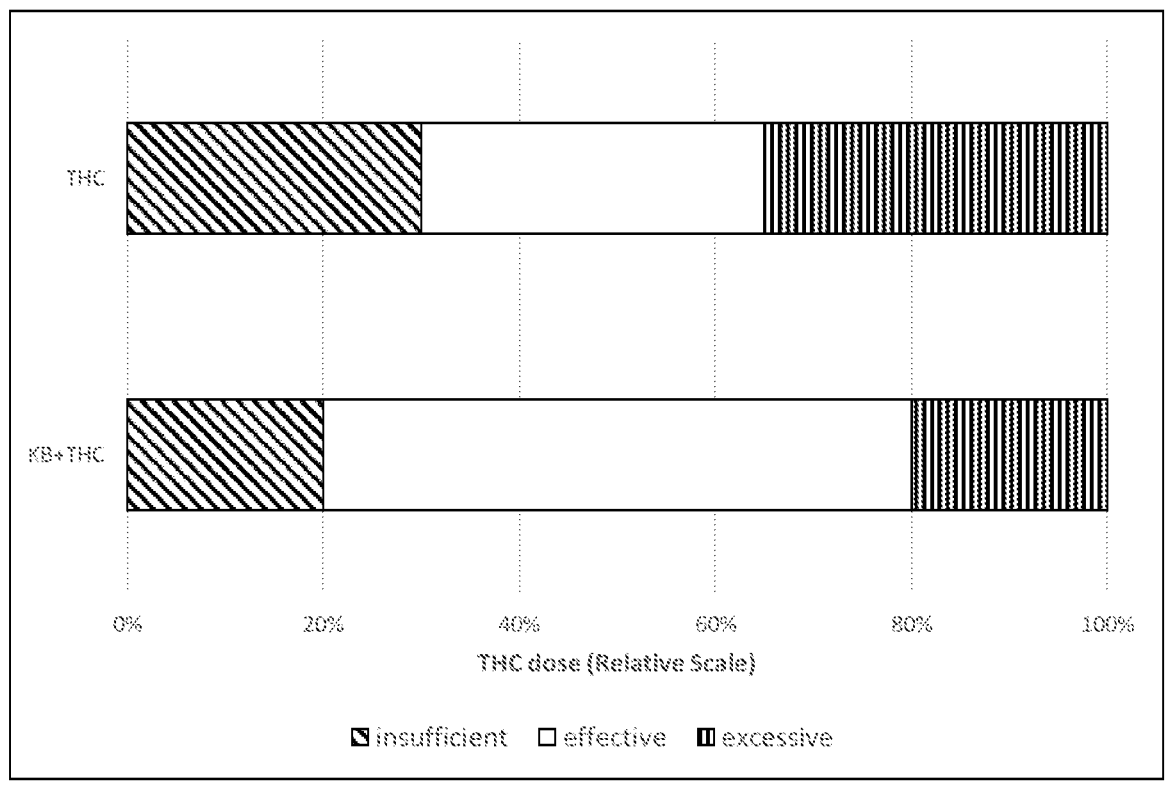
FIG. 3 schematically illustrates expected effectiveness at different THC dosage levels comparing a composition of ketone bodies and THC to a composition of THC without ketone bodies, showing that the composition comprising ketone bodies and THC has a broader range of effective dosages than the composition of THC without ketone bodies.

FIG. 3 schematically illustrates the expected effectiveness at different THC dosage levels comparing a composition of ketone bodies and THC (KB+THC) to a composition of THC without ketone bodies (THC). THC levels too low to produce a desired effect are labeled as "insufficient," THC levels capable of producing a desired effect are labeled "effective," and THC levels which are too high (e.g., are anxiogenic, too disruptive to memory, and/or too disruptive of cardiovascular measures) are labeled "excessive." As shown, the ketannabis composition has a broader range of effective dosages than the THC without ketone bodies. Because the ketone bodies potentiate the utilization of THC, the positive effects may be realized at lower doses relative to the same amount of THC without ketone bodies. At the same time, the ketone bodies counteract one or more negative side effects of THC and thereby allow higher doses of THC before such negative side effects are excessive. Ketannabis compositions are therefore believed to expand the "sweet spot" of THC dosing by providing enhanced positive effects and/or reducing negative side effects.

The THC dose on the horizontal axes of FIGS. 1 through 3 is shown as a normalized, relative scale of 0 to 100. This scale may correspond to the THC dosage levels described elsewhere herein. In other words, the "100" level on the normalized scale may be equated to a THC dose of about 100 mg, with other values interpolated accordingly (e.g., 10% equates to 10 mg THC, 20% equates to 20 mg THC, etcetera).

In addition to the use of ketone bodies as a metabolic energy source, ketone bodies may also provide beneficial molecular signaling. As an example of beneficial molecular signaling, BHB may affect histone proteins, altering gene expression in beneficial ways such as by promoting expression of mitochondria enzymes related to oxidative phosphorylation and the electron transport chain, PPARα (a protein with the ability to speed up the breakdown of fat), and the like. Acetoacetate may have molecular signaling functions similar to those of BHB, as they are treated similarly in the body and since the body can readily convert between the two compounds.

Although many of the examples are described herein in the context of a subject being in a state of ketosis, it will be understood that realization of the beneficial effects does not necessarily require the subject to be in a state of ketosis. In other words, beneficial effects may be realized as a result of co-administration of the exogenous ketone body component and the THC. These effects may be further enhanced once the subject enters an active state of ketosis, and the exogenous ketone body component can itself aid in getting the subject into such a state, but ketosis is not necessarily a requirement for realizing these effects.

A. Reduction of THC Side Effects

As described above, despite THC's positive effects, THC is also associated with negative side effects including an increase in appetite, a disruption of working memory, anxiety, and changes to heart rate and/or blood pressure. When THC is combined with a ketone body component in a ketannabis composition or treatment method, one or more of these negative side effects may be beneficially countered.

1. Appetite

THC is infamously known for causing an increased appetite, and this is believed to be due at least in part to its activation of $CB_1$ receptors in the hypothalamus. $CB_1$ receptors are associated with release of ghrelin, the "hunger hormone." Though sometimes seen as a desired effect, increased appetite is often an undesirable side effect of THC consumption (Berry et al. "Tetrahydrocannabinol and endocannabinoids in feeding and appetite" Pharmacology and Therapeutics 95 (2) 185-190).

Exogenous ketone bodies, on the other hand, may cause appetite suppression. Ketone bodies provide a readily available fuel source for the body and the brain with rapid effects on satiety. Exogenous ketone body supplementation can also lower ghrelin levels, thereby suppressing appetite and perceived hunger. Further, when in a state of ketosis, energy levels are more balanced and regular as opposed to the highs and lows associated with a diet higher in carbohydrates. Cravings often occur during these energy lows (e.g., "sugar crashes") (Benton "Carbohydrate ingestion, blood glucose and mood" 26 (3) 293-308). These cravings are reduced or eliminated with exogenous ketone body supplementation.

The appetite regularization effects resulting from ketone body supplementation beneficially counter the increases in appetite normally related to THC consumption. It is expected that compared to a THC composition without ketone bodies, the appetite regularization effects of ketone bodies in a ketannabis composition allow for the administration of greater amounts of THC before reaching excessive appetite promotion or allow for the administration of similar amounts of THC with reduced occurrence of appetite promoting side effects. The combination of ketone bodies and THC therefore provides beneficial use and functionality not capable with either component individually.

2. Working Memory

THC is also known to impair short-term memory formation. It is thought that working memory impairment is related to THC's association with $CB_1$ receptors on astroglial cells of the brain, and particularly of the hippocampus (see Han et al. "Acute Cannabinoids Impair Working Memory through Astroglial $CB_1$ Receptor Modulation of Hippocampal LTC" Cell 2012).

In contrast, enhanced memory effects are associated with exogenous ketone body supplementation as well as with ketosis, which may be induced through the use of exogenous ketone bodies. When the brain switches from using glucose as its primary fuel source to using ketone bodies as its primary fuel source, the resulting metabolic state appears to dampen the level of impairment otherwise expected from THC consumption. Further, ketone body molecular signaling provides indirect antioxidant effects via endogenous enzyme upregulation. For example, BHB molecular signaling may be associated with Class I and II histone deacetylase (HDAC) inhibition (Huang et al. "The ketone body metabolite β-hydroxybutyrate induces an antidepression-associated ramification of microglia via HDACs inhibition-triggered Akt-small RhoGTPase activation" Glia 66(2) 256-278), which is related to mitigation of neurodegenerative diseases (e.g., Alzheimer's disease and Huntington's disease), and has positive effects on memory.

It is expected that compared to a THC composition without ketone bodies, the memory enhancing effects of ketone bodies in a ketannabis composition allow for the administration of greater amounts of THC before reaching excessive levels of memory disruption or allow for the administration of similar amounts of THC with reduced occurrence of memory-related side effects. The combination of ketone bodies and THC therefore provides beneficial use and functionality not capable with either component individually.

3. Anxiety

Though often one of the intended effects of THC is a state of relaxation and reduced stress, the opposite effect is also known to occur in some circumstances, causing anxiety and potentially even panic in the user.

In contrast, ketone body supplementation may be associated with a calming, anxiolytic effect. This may occur at least in part as a result of a more regularized metabolic state associated with ketone body supplementation and particularly when in ketosis. That is, the peaks and troughs in energy levels common to a glycolysis-based metabolic state can aggravate feelings of anxiety, whereas the steadier, more regularized energy levels associated with ketone bodies and ketosis can act as a "buffer" against anxiogenic triggers (Yamanshi "Beta-hydroxybutyrate, an endogenic NLRP3 inflammasome inhibitor, attenuates stress-induced behavioral and inflammatory responses" Nature 7, 1-10).

Ketone body molecular signaling can further provide beneficial anxiolytic/anti-depressant activity. For example, BHB molecular signaling may be associated with Class I and II histone deacetylase (HDAC) inhibition, which has positive effects on mood, among other effects. BHB may also increase synthesis of gamma-Aminobutyric acid (GABA) in the brain, thereby promoting a calming, anxiolytic effect.

It is expected that compared to a THC composition without ketone bodies, the anxiolytic effects of ketone bodies in a ketannabis composition allow for the administration of greater amounts of THC before reaching excessive levels of anxiety or allow for the administration of similar amounts of THC with reduced occurrence of anxiogenic side effects. The combination of ketone bodies and THC therefore provides beneficial use and functionality not capable with either component individually.

4. Cardiovascular Health

THC use may also be associated with an increase in heart rate and/or disruption to normal blood pressure. Although these effects may not be overly concerning for young, healthy users, they may be particularly concerning for those with cardiovascular disease. For such users, THC can aggravate underlying health risks by increasing cardiac work, increasing catecholamine levels, and impairing blood oxygen carrying capacity (see Jones "Cardiovascular system effects of marijuana" J. Clin. Pharmacol. 42 (11): 58-63).

Exogenous ketone bodies may aid in regulating blood pressure and/or improving cardiovascular health, and additionally may induce a sustained state of ketosis to further promote these effects. Ketosis can reduce the retention of sodium ions associated with high blood pressure. The lowered insulin release associated with ketosis (Paoli et al. "Beyond weight loss: a review of the therapeutic uses of very-low-carbohydrate (ketogenic) diets" European Journal of Clinical Nutrition 67, 789-796) may also correspond to better regulated blood pressure.

Ketone body molecular signaling can further provide beneficial cardiovascular effects. For example, BHB may act as an agonist of the $HCA_2$ protein. As with high-dose niacin supplementation, this is associated with anti-inflammatory effects in a variety of tissues including vascular tissue. It is also associated with increasing levels of HDL cholesterol, reducing atherogenic activity, and promoting beneficial vasodilation.

It is expected that compared to a THC composition without ketone bodies, the cardiovascular effects of ketone bodies in a ketannabis composition allow for the administration of greater amounts of THC before reaching excessive levels of cardiovascular problems or allow for the administration of similar amounts of THC with reduced occurrence of negative cardiovascular side effects. The combination of ketone bodies and THC therefore provides beneficial use and functionality not capable with either component individually.

B. Reduction of Ketone Body Side Effects

Although supplementation with exogenous ketone bodies has multiple benefits, it can also be associated with one or more undesirable side effects. In particular, ketone body supplementation may be associated with keto flu symptoms when used to try to achieve a state of ketosis. Ketone body supplementation may also aggravate depressive symptoms as a result of disruption to serotonin production.

1. Keto Flu

Exogenous ketone bodies may be taken to induce a metabolic state of ketosis. As described above, the transition from a metabolic state where glucose is the primary fuel source to one in which ketone bodies are the primary fuel source is often associated with uncomfortable symptoms related to hypoglycemia and the body's entry into an energy-saving mode. These symptoms lessen over time as the body becomes more efficient at utilizing fat to generate ketone bodies and at using the generated ketone bodies as its primary fuel source. However, the difficulties involved in the transition period cause many users who could otherwise benefit from a ketogenic diet to give up.

A ketannabis composition can beneficially reduce the duration and/or severity of the unpleasant keto flu symptoms and can therefore also promote greater user compliance to a ketogenic diet. The THC component can provide beneficial antiemetic (anti-nausea) activity (see Anderson et al. "Delta-9-tetrahydrocannabinol as an atiemetic" Am. J. Hosp. Pharm. 1981 May; 38(5): 639-46), which is particularly beneficial during bouts of keto flu symptoms. The analgesic and the psychoactive, euphoric effects of THC also act to reduce the severity of keto flu symptoms and make the transition from a glycolytic state to a ketogenic state easier for the user.

It is expected that compared to ketone body supplementation without THC, the keto flu symptoms associated with supplementation of a ketannabis composition are markedly reduced. This beneficially enables an easier transition to a state of ketosis and allows a greater number of users to successfully achieve a desired state of ketosis. The combination of ketone bodies and THC therefore provides beneficial use and functionality not capable with either component individually.

2. Depressive Symptoms

Many individuals report a reduction in depressive symptoms as a result of a ketogenic diet, most likely due to general increases in physiological health. However, some individuals may experience an increase in symptoms of depression during ketosis because of difficulties in producing the neurotransmitter serotonin. Low serotonin levels are associated with depression and anxiety. Serotonin is derived from the essential amino acid tryptophan, which must be consumed in the diet. Tryptophan has a better likelihood of passing the blood-brain barrier, where it can be converted to serotonin, when it is at a higher blood concentration relative to other proteins and amino acids. When insulin is released, it functions to "pull" these other proteins and amino acids into muscles, leaving a higher proportion of tryptophan remaining in the blood to cross the blood-brain barrier. With a low-carb ketogenic diet, however, lower carbohydrate intake means less insulin is released. Thus, although a ketogenic diet includes an abundance of tryptophan, less tryptophan will cross the blood-brain barrier to be available for serotonin production because it must compete with other protein components in the blood.

The psychoactive effects of THC can therefore complement the supplementation of exogenous ketone bodies by counteracting the potential negative effects related to low serotonin production. THC readily crosses the blood-brain barrier and may therefore be available to maintain sufficient activation of serotonin receptors in the brain, even while a ketogenic diet is maintained. In addition, cannabinoids such as THC may act to modulate GABA and/or GABA receptor activity. Ketone bodies such as BHB and acetoacetate may also be involved in GABA receptor signaling, and may function synergistically with THC and/or other cannabinoids to modulate GABA and/or GABA receptor activity.

It is expected that compared to ketone body supplementation without THC, the depressive symptoms associated with supplementation of a ketannabis composition are markedly reduced. The combination of ketone bodies and THC therefore provides beneficial use and functionality not capable with either component individually.

C. Enhancement of Positive Effects

Supplementation of exogenous ketone bodies in combination with THC can beneficially enhance the positive effects of ketone bodies and/or the positive effects of THC. As described above, and as schematically illustrated in FIG. 1, the euphoric psychoactive effects of THC may be enhanced as a result of co-administration with exogenous ketone bodies. Various other beneficial physiological effects can also result from combined administration, including neuroprotection, anti-inflammation, analgesic effects, anti-oxidant effects, anti-tumorigenic effects, and anti-aging effects.

1. Neuroprotection

Neuroprotection and enhanced memory are effects associated with exogenous ketone body supplementation as well as with ketosis, which may be induced by the use of exogenous ketone bodies. When the brain switches from using glucose as its primary fuel source to using ketone bodies as its primary fuel source, the resulting metabolic state provides additional protection against neurodegenerative conditions such as epilepsy and possibly Alzheimer's and Parkinson's diseases (see, e.g., Gasior et al. "Neuroprotective and disease-modifying effects of the ketogenic diet" Behav. Pharmacol. 2006 September; 17 (5-6): 431-39).

Ketone bodies, in particular BHB, are potent free radical scavengers and provide direct antioxidant effects. Because the brain actively utilizes ketone bodies when they are available, the relatively high concentration of ketone bodies in the brain following supplementation therefore provides an effective antioxidant neuroprotective function. Further, BHB molecular signaling provides indirect antioxidant effects via endogenous enzyme upregulation. For example, BHB molecular signaling may be associated with Class I and II histone deacetylase (HDAC) inhibition, which is related to mitigation of neurodegenerative diseases (e.g., Alzheimer's disease and Huntington's disease), among other effects. BHB may also increase gene expression of various endogenous defense proteins such as reactive oxygen species (ROS) scavengers like catalase and SOD2, and toxic metal scavengers such as metallothionein. BHB may also act as an agonist of the $HCA_2$ protein. As with high-dose niacin supplementation, this is associated with anti-inflammatory effects in a variety of tissues including the brain.

Despite its temporary disruption of short-term memory, THC may provide a net neuroprotective effect. In particular, THC has been shown to protect against glutamate toxicity (see Hampson et al. "Cannabidiol and (–)$\Delta^9$-tetrahydrocannabinol are neuroprotective antioxidants" Proc. Natl. Acad. Sci. USA, 1998 Jul. 7; 95(14): 8268-73). THC provides antioxidant properties and can readily cross the blood-brain barrier to further provide neuroprotective activity.

It is expected that the neuroprotective effects of THC and ketone bodies are synergistically enhanced as a result of their combined administration. It is expected that the resulting neuroprotective effects will be greater than that possible with either component alone and/or will be greater than the sum of the effects of each component when used independently. The beneficial neuroprotective effects of a ketannabis composition may be particularly useful in treating and/or managing Alzheimer's disease, Parkinson's disease, and epilepsy, for example.

2. Anti Inflammation/Analgesic

THC may provide an anti-inflammatory effect by modulating immune system functions of the ECS. Both $CB_1$ and $CB_2$ receptors have been found on immune cells, suggesting that endocannabinoids play an important role in immune system regulation (see Nagarkatti et al. "Cannabinoids as novel anti-inflammatory drugs" Ruture Med. Chem. 2009 October; 1(7): 1333-49). THC is believed to mimic endocannabinoids such as anandamide in a way that reduces excessive inflammation.

Exogenous ketone body supplementation may also reduce inflammation. When under ketone body supplementation and/or when in ketosis, less insulin is produced, there is a reduction in inflammation markers, and there is a reduction in the generation of free radicals, which are known to contribute to inflammation. Ketone bodies also increase levels of adenosine, which is known to reduce inflammation and reduce pain.

Ketone body molecular signaling can further provide beneficial anti-inflammatory activity. For example, BHB molecular signaling may be associated with Class I and II histone deacetylase (HDAC) inhibition, which is related to inflammation control among other effects. BHB also activates the AMPK pathway, which decreases inflammation and pain, and also inhibits the COX-2 enzyme in a manner somewhat similar to conventional non-steroidal anti-inflammatory drugs. BHB also inhibits the NLRP3 inflammasome, which is the pathway involved in initiating the inflammatory response. BHB may also act as an agonist of the $HCA_2$ protein. As with high-dose niacin supplementation, this is associated with anti-inflammatory effects in a variety of tissues including the brain, gastrointestinal tract, skin, and vascular tissue.

Although the anti-inflammatory properties discussed above may themselves lead to reductions in pain, the combined administration of THC and ketone bodies is also expected to reduce perceptions of pain through one or more mechanisms independent of inflammation reduction. For example, THC's psychoactive effects may mediate pain perception in a manner independent of any anti-inflammatory effects.

It is expected that the anti-inflammatory and analgesic effects of THC and ketone bodies are synergistically enhanced as a result of their combined administration. The ketone body component of the composition is expected to lead to reductions in inflammation by way of reduced reactive oxygen species and increased levels of adenosine, for example, and these effects may be further enhanced as a result of the ketone bodies inducing or sustain ketosis in the subject. The THC component is meanwhile expected to further reduce excessive inflammation and pain through its effects on endocannabinoid receptors. It is expected that the resulting anti-inflammatory and analgesic effects will be greater than that possible with either component alone and/or will be greater than the sum of the effects of each component when used independently. For example, a ketannabis composition with a given level of THC can provide more pain relief than the same amount of THC without a ketone body component. Likewise, a ketannabis composition may be able to provide the same amount of pain relief, with less THC, as a higher THC dose without a ketone body component. This allows for easier administration and dosing for pain management, since the user will be able to achieve greater analgesic effects for given THC levels.

3. Anti-Tumorigenic

THC supplementation may provide beneficial anti-tumorigenic effects through multiple mechanisms (see, e.g., "NTP Toxicology and Carcinogenesis Studies of 1-Trans-Delta(9)-Tetrahydrocannabinol (CAS No. 1972-08-3) in F344 Rats and B6C3F1 Mice (Gavage Studies)" Natl. Toxicol. Program Tech. Rep. Ser. 1996 November; 446: 1-317) (see also National Cancer Institute "Cannabis and Cannabinoids (PDQ)—Health Professional Version," section titled "Antitumor Effects").

Ketone body supplementation may also be associated with anti-tumorigenic effects. For example, BHB molecular signaling may increase gene expression of endogenous defense proteins such as FOXO3, which is a tumor inhibitor. Such supplementation may also increase the expression of other endogenous defense proteins such as catalase, SOD2, and toxic metal scavengers such as metallothionein. Enhanced levels of these proteins can reduce tumor incidence. The enhanced autophagy associated with ketone body supplementation can also limit the ability of tumors to take hold (see Finn et al. "Ketone bodies stimulate chaperone-mediated autophagy" J. Biol. Chem. 2005 Jul. 8; 280 (27): 25864-70).

Further, cancerous tumor cells are characterized by an increased glucose demand relative to normal, healthy cells, and thus are less able to effectively utilize ketone bodies for energy. A shift away from glucose as the primary cellular energy source and toward ketone bodies may therefore inhibit cancer progression (see, e.g., Poff et al. "Ketone supplementation decreases tumor cell viability and prolongs survival of mice with metastatic cancer" Int. J. Cancer 2014 Oct. 1; 135(7): 1711-20).

The anti-tumorigenic effects of THC and exogenous ketone body supplementation are expected to be synergistically enhanced as a result of their combined administration. It is expected that the anti-tumorigenic effects of a ketannabis composition will be greater than that possible with either component alone and/or will be greater than the sum of the effects of each component when used independently.

In some embodiments, a ketannabis composition may be administered in conjunction with cancer treatment such as radiation therapy and/or chemotherapy. Patients undergoing such treatment often suffer from intense nausea and pain (particularly with chemotherapy), and fatigue (particularly with radiation therapy). At the same time, such patients often have very little appetite. A ketannabis composition can beneficially assist in alleviating one or more of these negative effects while also promoting the efficacy of the cancer treatment due to the associated reduction in glycolysis. As described above, cancer cells typically rely much more on glucose consumption than normal, healthy cells, and have greater difficulty utilizing ketone bodies as an energy source.

As described above, the ketone body component of the ketannabis composition tends to somewhat curb the appetite increasing effects of the THC component. For a normal, healthy individual, this beneficially lessens the "munchies" effect that is otherwise commonly associated with consumption of high carbohydrate foods. On the other hand, a patient undergoing cancer treatment will often have a baseline appetite that is already low. For such a patient, increasing appetite is desirable. At the same time, however, the high carbohydrate foods typically associated with THC-induced increases to appetite do not complement chemotherapy and/or radiation therapy the same way a ketogenic diet does. Beneficially, administration of a ketannabis composition to such patients will tend to raise and normalize appetite levels without excessively raising and driving it toward high carbohydrate foods. Appetite can therefore be increased to a healthier level while also keeping it within levels where a ketogenic diet, rather than a glycogenic diet, may be more easily maintained.

4. Anti-Aging/Longevity

The ability of THC to modulate the ECS can promote longevity in the user. Disruptions in the ECS can increase with age, and the ECS may therefore be a suitable therapeutic target for age-related conditions (see, e.g., Bilkei-Gorzo et al. "A chronic los dose of $\Delta^9$-tetrahydrocannabinol (THC) restores cognitive function in old mice" Nature Medicine 23, 782-787). THC also has potent antioxidant and anti-inflammatory properties, as described elsewhere herein, which further function to reduce the effects of aging.

Ketone body supplementation may also be associated with longevity promoting effects. As discussed above, ketone body supplementation can positively influence mitochondrial health, including raising the number of mitochondria and raising the concentration of antioxidants in the mitochondria to prevent reactive oxygen species (ROS) damage to the mitochondria. BHB may also stimulate chaperone-mediated autophagy of certain proteins marked by BHB oxidative modification (see Finn et al. "Ketone bodies stimulate chaperone-mediated autophagy" J. Biol. Chem. 2005 Jul. 8; 280(27): 25864-70).

The longevity promoting effects of CBD and exogenous ketone body supplementation are expected to be synergistically enhanced as a result of their combined administration. It is expected that the longevity effects of a ketannabis composition will be greater than that possible with either component alone and/or will be greater than the sum of the effects of each component when used independently. Longevity is of course a multifaceted issue, and the longevity enhancing effects of ketannabis supplementation may be further promoted by other beneficial effects described herein, such as neuroprotection, antioxidant effects, and anti-inflammatory effects.

IV. Dosage Forms and Administration

The ketannabis composition may be administered in various ways including oral, intragastric, nasal or pulmonary, as an injectable (e.g., subdermal, parenteral, or intravenous), as a suppository, etcetera.

In some embodiments, the ketannabis composition may be provided as a solid or powder form. Solid or powder ketogenic compositions may include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

In alternative embodiments, the ketannabis composition may be provided as a liquid, such as in the form of a shot or mouth spray for fast delivery and absorption, or as a gel. Liquid or gel forms may include one or more carriers, such as water, ethanol, glycerin, propylene glycol, 1,3-propandiol, and the like, into which the components are dissolved or dispersed. The composition may include flavoring agents that help mask the somewhat poor taste of BHB compounds. These flavoring agents may include essential oils, such as peppermint, natural and artificial sweeteners, and other flavorants known in the art.

The ketannabis composition may include one or more supplements known in the art, such as vitamins, minerals, and caffeine or other stimulants. For example, caffeine may be included in an amount of about 10 mg to about 300 mg per dose, or about 25 mg to about 250 mg per dose, or about 40 mg to about 200 mg per dose, or about 50 mg to about 150 mg per dose.

The ketannabis compositions described herein may be provided within a dosage regimen effective in inducing and sustaining ketosis and/or providing other benefits described herein. For example, the mass of exogenous ketone bodies in a daily dose (for an average adult of about 175 lbs.) may range from about 0.5 grams to about 50 grams, or about 1 gram to about 40 grams, or about 2 grams to about 30 grams, or about 3 grams to about 25 grams, or about 4 grams to about 20 grams, and may be provided using one or more unit doses. The mass of the THC component in a daily dose (for an average adult of about 175 lbs.) may range from about 1 mg to about 500 mg, or about 5 mg to about 400 mg, or about 10 mg to about 300 mg, or about 15 mg to about 250 mg, or about 20 mg to about 200 mg, or about 25 mg to about 150 mg, and may be provided using one or more unit doses. As needed, dosages may be adjusted (e.g., linearly) based on weight of the subject. The THC component and the ketone body component may be mixed/combined, though some methods may provide the components separately. The daily dose(s) may be taken as a single daily dose or as multiple doses (e.g., 2, 3, or 4 times daily).

The ratio of THC component to ketone body component in the ketannabis composition may be adjusted and customized according to particular user needs. For example, a patient undergoing cancer treatment may prefer a relatively higher level of THC in order to lean more towards the appetite increasing and analgesic effects of THC. On the other hand, an individual without chronic pain and/or inflammation issues may prefer a ketannabis composition with relatively less THC. For example, a typical ketannabis composition may include about 5-15 mg THC per gram ketone bodies. This ratio may be adjusted to a more "THC-rich" ketannabis composition including, for example, about 20, 40, 60, 80, or 100 mg THC per gram ketone bodies (or a range using the foregoing as endpoints). Alternatively, the ratio may be adjusted to a more "ketone body rich" ketannabis composition including, for example, 0.25, 0.5, 1, or 3 mg THC per g ketone bodies (or a range using the foregoing as endpoints).

In a preferred embodiment, a ketogenic composition is administered in one or more unit doses per day via oral administration of the composition in a solid, powdered form or liquid, such as in a powdered mixture (e.g., powder filled gelatin capsules), hard-pressed tablets, or other oral administration route known to those skilled in the art.

In some embodiments, multiple doses of the composition are administered. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etcetera.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo. In accordance with the present disclosure, a suitable single dose size is a dose that is capable of preventing or alleviating (reducing or eliminating) a symptom in a patient when administered one or more times over a suitable time period (e.g., a daily dose).

The amount of composition administered will depend on potency, absorption, distribution, metabolism, and excretion rates of the composition components, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once over a given time period (e.g., once per day), or may be divided and administered over intervals of time. It is to be understood that administration may be adjusted according to individual need and professional judgment of a person administrating or supervising the administration of the compositions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition comprising:
   a ketone body component;
   a tetrahydrocannabinol (THC) component; and
   a pharmaceutically or dietetically acceptable carrier,
   wherein the THC component includes a THC compound having a BHB or acetoacetate attached to the THC via an ester bond.

2. The composition of claim 1, wherein the ketone body component is selected from the group consisting of beta-hydroxybutyrate (BHB) salts, BHB esters, beta-hydroxybutyric acid, acetoacetate salts, acetoacetate esters, acetoacetic acid, and combinations thereof.

3. The composition of claim 2, wherein the ketone body component includes a BHB salt or ester and/or acetoacetate salt or ester.

4. The composition of claim 1, further comprising one or more additional cannabinoid compounds derived from the cannabis plant.

5. The composition of claim 1, wherein the composition omits CBD.

6. The composition of claim 1, further comprising one or more of 1,3-butanediol, a fatty acid, or an ester of a fatty acid.

7. The composition of claim 6, wherein the fatty acid or ester thereof is a medium chain fatty acid or ester thereof, or a short chain fatty acid or ester thereof.

8. The composition of claim 1, wherein the composition is provided in solid or powder form.

9. The composition of claim 1, wherein the composition is provided in liquid form.

10. The composition of claim 1, wherein the composition is in a dosage form that provides more than 2 grams of available ketone bodies.

11. The composition of claim 1, wherein the composition is in a dosage form that provides about 5 mg to about 400 mg of available THC.

12. The composition of claim 1, wherein the composition is formulated to provide euphoric effects of the THC component in a mammal in addition to raising blood ketone level.

13. The composition of claim 1, wherein the composition is in a dosage form configured for oral, intragastric, nasal, pulmonary, parenteral, intravenous, intra-arterial, or injectable delivery.

14. The composition of claim 13, wherein the dosage form is formulated to deliver a ratio of biologically available ketone bodies to biologically available THC of at least 50:1.

15. A composition comprising:
   a ketone body component;
   a tetrahydrocannabinol (THC) component; and
   a pharmaceutically or dietetically acceptable carrier,
   wherein the THC component includes a THC compound having a BHB or acetoacetate attached to the THC via an ester bond, and
   wherein the composition is formulated to deliver therapeutically effective amounts of both ketone bodies and THC in a ratio of biologically available ketone bodies to biologically available THC of at least 10:1 when the composition is administered to a mammal.

16. The composition of claim 15, wherein the composition is in a dosage form configured for oral, intragastric, nasal, pulmonary, parenteral, intravenous, intra-arterial, or injectable delivery.

17. The composition of claim 15, wherein the composition is an oral dosage form.

18. A kit for administering ketone bodies and THC to a subject, comprising:
    a composition as in claim 15;
    a container in which the composition is placed; and
    a measuring device configured to hold therein a unit dose, or fraction thereof, of the composition.

19. A composition comprising:
    an amount of a ketone body component;
    an amount of a tetrahydrocannabinol (THC) component that provides euphoric effects of the THC component in a mammal; and
    a pharmaceutically or dietetically acceptable carrier,
    wherein the THC component includes a THC compound having a BHB or acetoacetate attached to the THC via an ester bond,
    wherein the composition is in a dosage form designed to provide both a biologically available amount of the ketone body component and a biologically available amount of the THC component sufficient to provide euphoric effects when the dosage form is administered to the mammal, and
    wherein the dosage form is designed to deliver a biologically available ratio of the ketone body component to the THC component of at least 10:1.

20. The composition of claim 19, wherein the ketone body component is selected from the group consisting of beta-hydroxybutyrate (BHB) salts, BHB esters, acetoacetate salts, acetoacetate esters, and combinations thereof.

21. The composition of claim 19, wherein the composition is an oral dosage form.

22. A composition comprising:
    a ketone body component comprising beta-hydroxybutyrate (BHB);
    a tetrahydrocannabinol (THC) component; and
    a pharmaceutically or dietetically acceptable carrier in a dosage form configured for oral, intragastric, nasal, pulmonary, intravenous, intra-arterial, or injectable delivery,
    wherein the THC component includes a THC compound having a BHB or acetoacetate attached to the THC via an ester bond, and
    wherein the pharmaceutically or dietetically acceptable carrier is designed to simultaneously provide biologically available amounts of both the ketone body component and the THC component to a subject when the dosage form is administered to the subject.

23. The composition of claim 22, wherein the ketone body component is selected from the group consisting of beta-hydroxybutyrate (BHB) salts, BHB esters, and combinations thereof.

24. A composition comprising:
    a ketone body component;
    a tetrahydrocannabinol (THC) component; and
    a pharmaceutically or dietetically acceptable carrier,
    wherein the THC component includes a THC compound having a BHB or acetoacetate attached to the THC via an ester bond,
    wherein the composition is formulated to deliver 1 mg to 500 mg of available THC and 0.5 gram to 50 grams of biologically available ketone bodies to a mammal in order to provide a therapeutically effective amounts of both THC and ketone bodies when the composition is administered to the mammal, and
    wherein the composition has a ratio of biologically available ketone bodies to biologically available THC of at least 10:1.

* * * * *